United States Patent [19]

Dohm et al.

[11] Patent Number: 5,720,391
[45] Date of Patent: Feb. 24, 1998

[54] PACKAGING AND HOLDER FOR HEART VALVE PROSTHESIS

[75] Inventors: Neil P. Dohm, Inver Grove Heights; Constance L. Roos, Woodbury, both of Minn.

[73] Assignee: St. Jude Medical, Inc., St. Paul, Minn.

[21] Appl. No.: 623,687

[22] Filed: Mar. 29, 1996

[51] Int. Cl.⁶ ................................. A61B 17/06
[52] U.S. Cl. ............... 206/438; 206/363; 206/583
[58] Field of Search ...................... 206/428, 363, 206/583; 623/2, 900

[56] References Cited

U.S. PATENT DOCUMENTS

| | | |
|---|---|---|
| 4,011,947 | 3/1977 | Sawyer . |
| 4,101,031 | 7/1978 | Cromie . |
| 4,182,446 | 1/1980 | Penny . |
| 4,211,325 | 7/1980 | Wright . |
| 4,512,471 | 4/1985 | Kaster et al. . |
| 4,542,825 | 9/1985 | Thomas et al. . |
| 4,585,453 | 4/1986 | Martin et al. . |
| 4,679,556 | 7/1987 | Lubock et al. . |
| 4,697,703 | 10/1987 | Will . |
| 4,750,619 | 6/1988 | Cohen et al. . |
| 4,801,015 | 1/1989 | Lubock et al. . |
| 5,148,920 | 9/1992 | Walker . |
| 5,236,450 | 8/1993 | Scott ................................. 673/2 |
| 5,386,908 | 2/1995 | Sinn . |
| 5,403,305 | 4/1995 | Sauter et al. . |
| 5,405,005 | 4/1995 | White . |
| 5,443,502 | 8/1995 | Caudillo et al. . |
| 5,447,230 | 9/1995 | Gerondale . |
| 5,560,487 | 10/1996 | Starr ................................. 206/438 |

Primary Examiner—Bryon P. Gehman
Attorney, Agent, or Firm—Hallie A. Finucane, Esq.

[57] ABSTRACT

Packaging and a holder is provided for a heart valve prosthesis. The holder is adapted to grasp the heart valve prosthesis and includes a post. The packaging includes a collar for holding the post of the holder. An inner tray of the packaging receives the collar such that the prosthesis is suspended within the inner tray. An outer tray receives the inner tray. An inner tray lid seals the inner tray and an outer tray lid seals the outer tray.

33 Claims, 6 Drawing Sheets

PACKAGING AND HOLDER FOR HEART VALVE PROSTHESIS

FIELD OF THE INVENTION

The present invention relates to packaging and a holder for a heart valve prosthesis. More particularly, the present invention relates to sterile packaging for a heart valve prosthesis.

BACKGROUND OF THE INVENTION

Heart valve prostheses are used to replace the natural heart valve of a patient. One type of heart valve prosthesis is shown in U.S. Pat. No. 4,276,658, issued Jul. 7, 1981, entitled HEART VALVE PROSTHESIS. Following manufacture and prior to implantation, the prosthesis must be transported in a sterile, heat sealed package. The package should be designed such that it is easily disassembled during surgery yet provides a secure, sterile and protective container during transportation.

Various packaging designs are shown in the prior art. For example, U.S. Pat. No. 4,101,031, issued Jul. 18, 1978 to Cromie, entitled "PACKAGE FOR PROSTHETIC HEART VALVE OR THE LIKE" shows a rigid canister which screws together and includes an O-ring. U.S. Pat. No. 4,512,471, issued Apr. 23, 1985 to Kaster et al., entitled "STORAGE UNIT" also shows a canister which screws together. The Cohen et al. reference U.S. Pat. No. 4,750,619, issued Jun. 4, 1988, entitled "PACKAGE WITH TRAY FOR SECURING AND PRESENTING A STERILE PROSTHETIC IMPLANT ELEMENT" shows three containers which sit within each other. The Lubock et al. reference, U.S. Pat. No. 4,801,015, issued Jan. 31, 1989 entitled "RELEASABLE HOLDER AND PACKAGE ASSEMBLY FOR A PROSTHETIC HEART VALVE" also shows a rigid container which screws together.

The heart valve prosthesis is typically suspended in the package by a holder. One such holder is described as a hanger in U.S. Pat. No. 5,443,502, issued Aug. 22, 1995 to Caudillo et al., entitled ROTATABLE HEART VALVE HOLDER. The holder should be constructed such that it may be held in the packaging.

SUMMARY OF THE INVENTION

The present invention provides packaging and a holder for a heart valve prosthesis. The packaging provides a sterile, heat sealed container for the heart valve prosthesis following manufacture, prior to implantation. The packaging includes an outer tray having a recess formed in it and a sealing flange. An inner tray has a recess formed in it and a sealing flange and is shaped to fit into the recess of the outer tray. A heart valve prosthesis holder is adapted to carry the heart valve prosthesis and fits into a collar. The collar is shaped to fit into the inner tray such that the heart valve prosthesis is suspended in the recess of the inner tray. An inner tray lid is sealed to the sealing flange of the inner tray and an outer tray lid is sealed to the sealing flange of the outer tray, thereby providing a heat seal. One aspect of the invention includes providing a post head on the heart valve prosthesis holder which is adapted to fit into the collar. In one embodiment, the post head includes at least two gripping portions such that the post head may be gripped by a surgeon to rotate the heart valve prosthesis during implantation. The gripping portions of the post head also prevent free rotation of the valve within the package.

BRIEF DESCRIPTION OF THE DRAWINGS

FIG. 9 is an exploded perspective view of packaging in accordance with another embodiment.

DETAILED DESCRIPTION OF THE PREFERRED EMBODIMENTS

Figure 1:
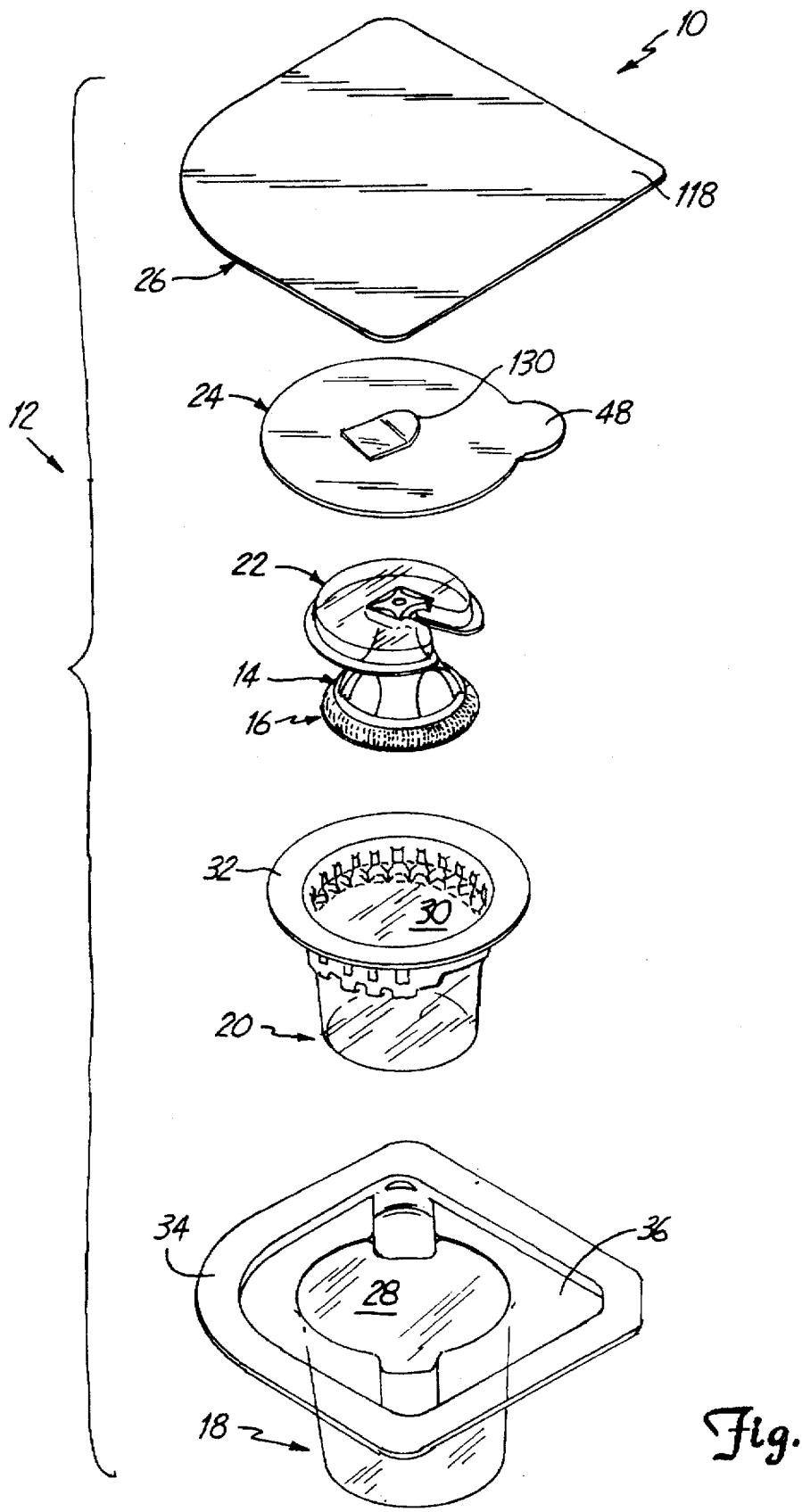
FIG. 1 is an exploded perspective view of the packaging in accordance with the present invention.

FIG. 1 is an exploded top perspective view of assembly 10 in accordance with the present invention. Assembly 10 includes packaging 12, valve holder 14 and heart valve prosthesis 16. Packaging 12 includes outer tray 18, inner tray 20, collar 22, inner tray lid 24 and outer tray lid 26.

As shown in FIG. 1, inner tray 20 fits into recess 28 of outer tray 18. Similarly, collar 22, heart valve prosthesis 16 and valve holder 14 fit in recess 30 of inner tray 20. Inner tray lid 24 fits over inner tray 20 and seals to inner tray sealing flange 32. Similarly, outer tray lid 26 fits over outer tray 18 and inner tray 20 and seals to outer tray sealing flange 34. Inner tray sealing flange 32 rests on flange shoulder 36 of outer tray 18 thereby supporting inner tray 20. FIGS. 2 through 7 describe the preferred embodiment and show how individual pieces fit together and advantageously cooperate.

Figure 2:
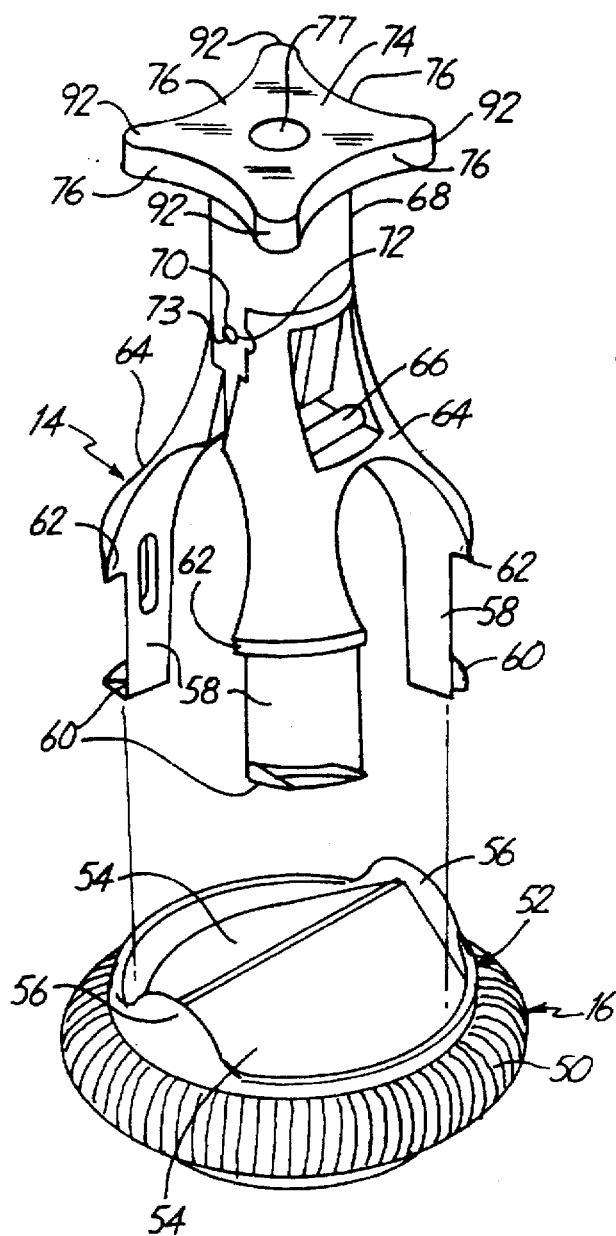
FIG. 2 is an exploded perspective view of a holder in accordance with the present invention and a heart valve prosthesis.

FIG. 2 is an exploded view of valve holder 14 and heart valve prosthesis 16. Prosthesis 16 includes suture cuff 50, prosthesis body 52 and occluders 54. Occluders 54 are supported by pivot guards 56 positioned on opposing sides of occluders 54. Valve holder 14 includes holder jaws 58 having jaw tips 60. Jaws 58 also include orifice engagement ridges 62. Jaws 58 are carried on two separate moveable members 64 which pivot about on pivots 66 and are pivotably connected to holder post 68. Post 68 includes alignment ridges 70 which fit into alignment grooves 72 of members 64. Post 68 includes post head 74 having four circumferentially spaced finger recesses or grips 76 and provides a generally square shape. Other shapes are within the scope of the present invention. A threaded receptacle 77 extends through the axis of post 68. Jaws 58 are adapted to fit through the annulus formed by body 52 and grip body 52 between tips 60 and orifice engagement ridges 62. Prosthesis 16 is released from valve holder 14 by inward movement of tips 60 about pivots 66. A suture (not shown) is used to secure jaws 58 in the position shown in FIG. 1 such that valve holder 14 is secured to prosthesis 16. The suture extends through suture hole 73 of post 68 and then around the upper portion of members 64 to secure and hold members 64 flush with post 68.

Figure 3B:
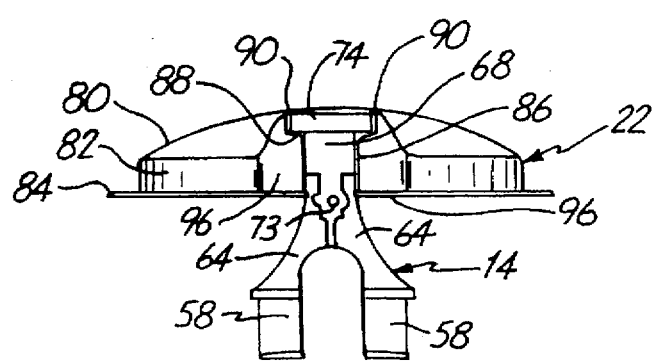
FIG. 3B is side plan view of the collar of FIG. 3A shown holding a holder.
Figure 3A:
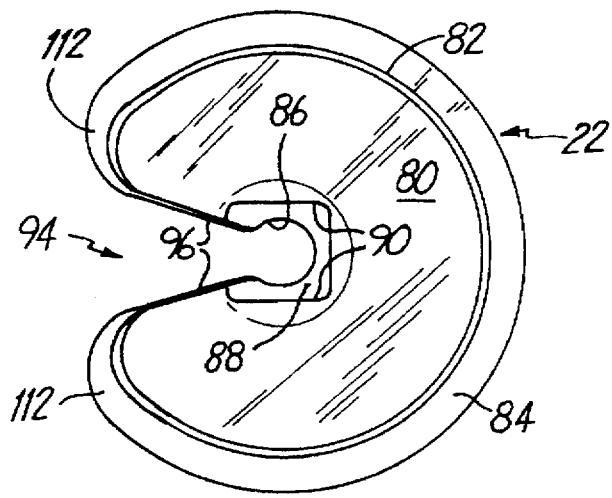
FIG. 3A is a top plan view of a collar used in accordance with the present invention.

FIG. 3A is a top plan view of collar 22. FIG. 3B is a side elevational view of collar 22 shown engaging valve holder 14. Collar 22 includes top concave portion 80, collar side wall 82 and collar lip 84. Holder post 68 fits into post clamp 86 formed in the center of collar 22. The walls of post clamp 86 are configured around post 68 and provide structural rigidity. Post clamp 86 also engages a portion of members 64 thereby maintaining jaws 58 in an engaging position about pivots 66 such that valve holder 14 grips prosthesis 16. Collar 22 also includes post head support surface 88 and rotation stop walls 90. Post head support surface 88 is recessed from concave portion 80 and is positioned and shaped to support holder post head 74. Rotation stop walls 90 intercept post head tips 92 formed by the generally square design and thereby prevent rotation of valve holder 14 in collar 22. Collar 22 includes V portion 94 formed therein extending radially outward from post clamp 86. V portion 94 includes side walls 96. V portion 94 is adapted to receive post 68 therethrough such that post 68 can be positioned in post clamp 86. This V-shaped design allows for the "give" necessary to push the collar 22 into place within the inner tray 20. Further, as explained below, the V portion 94 prevents rotation of collar 22 within inner tray 20.

Figure 4A:
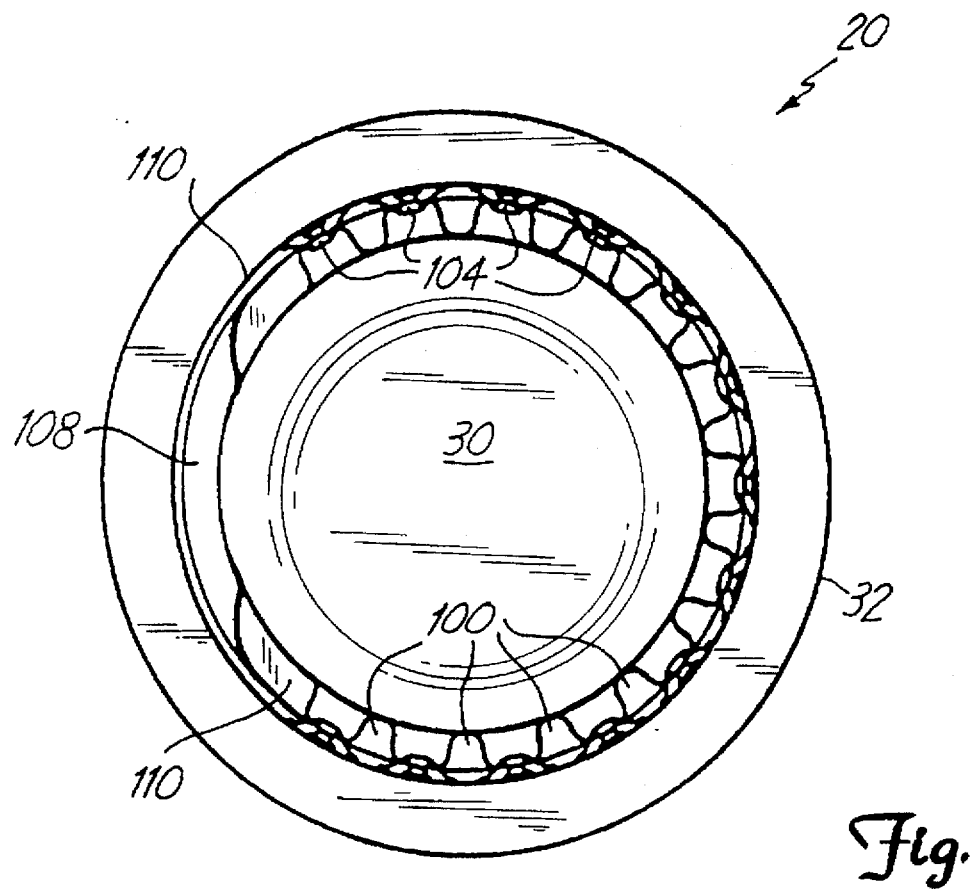
FIG. 4A is a top plan view and FIG. 4B is a side elevational view of an inner tray used in packaging in accordance with the invention.
Figure 4B:
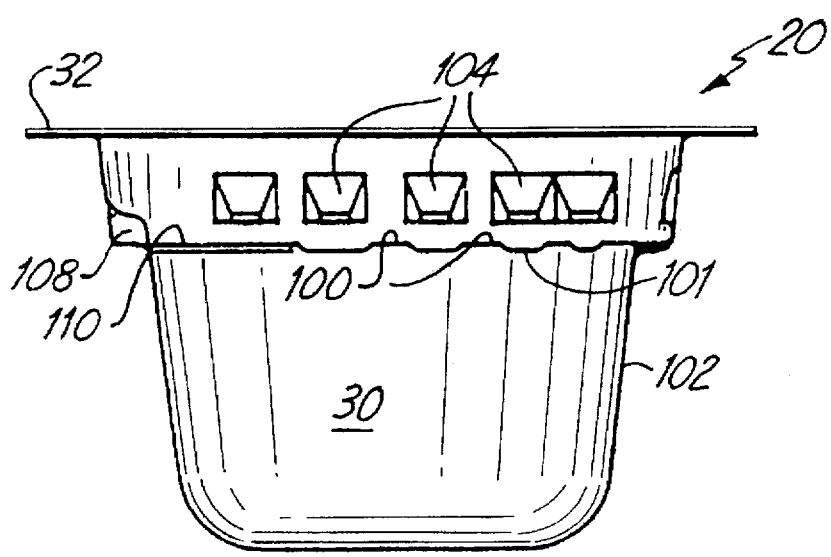

FIG. 4A is a top plan view and FIG. 4B is a side elevational view of inner tray 20. Inner tray 20 includes collar support surfaces or ledges 100. Collar support surfaces 100 are generally rectangular in shape, circumferentially interspersed, extend outward, and form a plurality of collar support ledges extending radially from wall 102 which forms a shelf for placement of lip 84 of collar 22. Ledges 101 alternate between collar support surfaces 100. Collar lock tabs 104 also extend radially from wall 102, are circumferentially interspersed, and are positioned above collar support surfaces 100 and ledges 101. Collar lock tabs 104 alternate between adjacent collar support surfaces 100. This allows tray 20 to be more easily formed through thermoform molding or other techniques. Inner tray 20 also includes middle ledge 108 positioned between key surfaces 110. Key lips 112 of collar 22 on either side of V portion 94 fit within key surfaces 110 and are separated by middle ledge 108. This prevents rotation of collar 22 in tray 20.

Figure 5A:
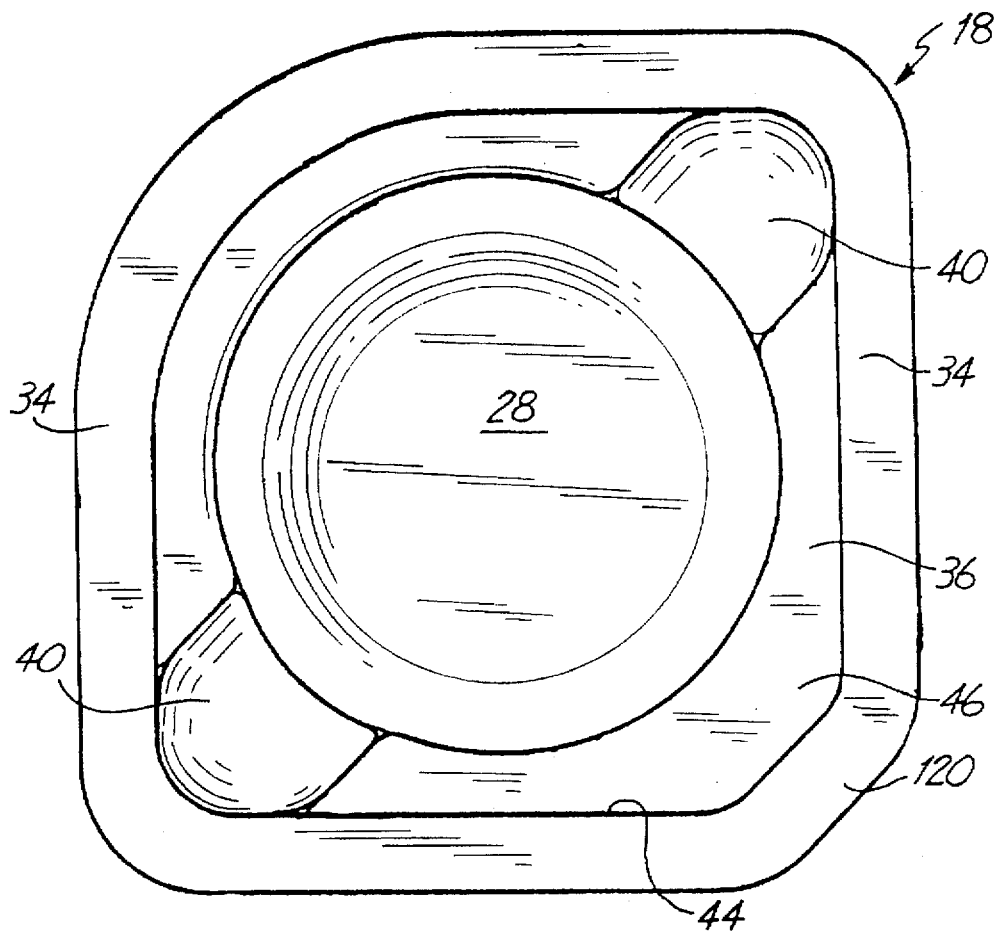
FIG. 5A is a top plan view and FIG. 5B is a side elevational view of an outer tray in accordance with the present invention.
Figure 5B:
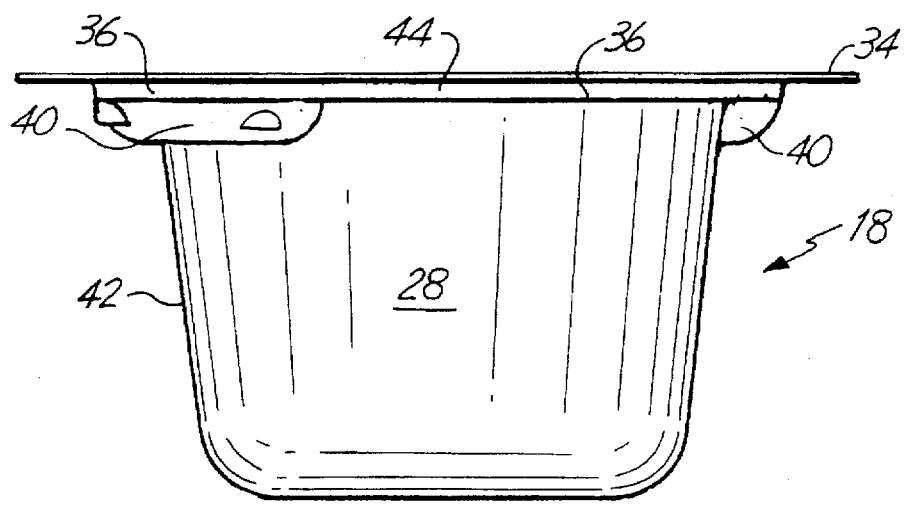

FIG. 5A is a top plan view and FIG. 5B is a side elevational view of outer tray 18. Outer tray 18 includes finger recesses 40 formed in flange shoulder 36 on opposite sides of recess 28. Recess 28 is formed by wall 42 and finger recesses 40 extend downward from shoulder 36. The depression formed by flange shoulder 36 forms lip inner wall 44 which extends between sealing flange 34 and flange shoulder 36. A portion of flange shoulder 36 forms tab receiving shoulder 46 for receiving tab 48 of inner lid 24. Flange shoulder 36 is shaped to support flange 32 of inner tray 20. With inner lid 24 sealed to flange 32, tab 48 fits in tab receiving shoulder 46. Further, outer tray lid 26 seals to sealing flange 34 and tab 118 extends over cut-away portion 120 of sealing flange 34. In one embodiment, lids 24 and 26 are heat sealed to trays 20 and 18, respectively, using a platen during manufacture.

Figure 6:
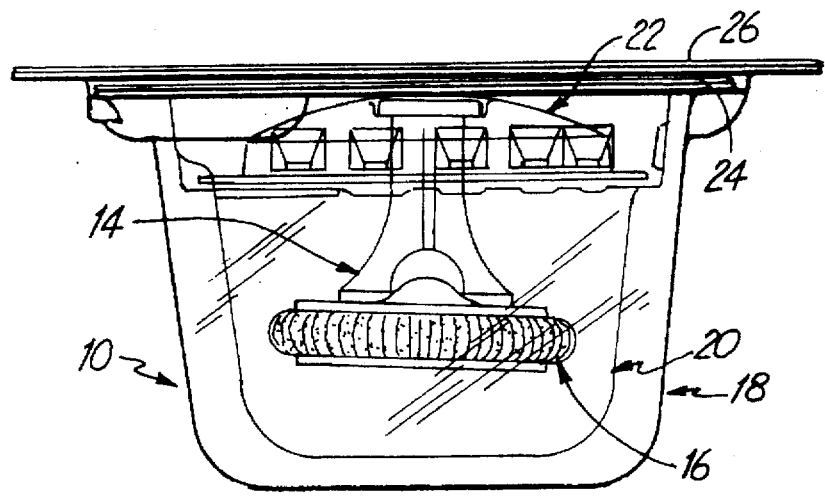
FIG. 6 is a side plan view of packaging in accordance with the present invention shown in an assembled condition.
Figure 7:
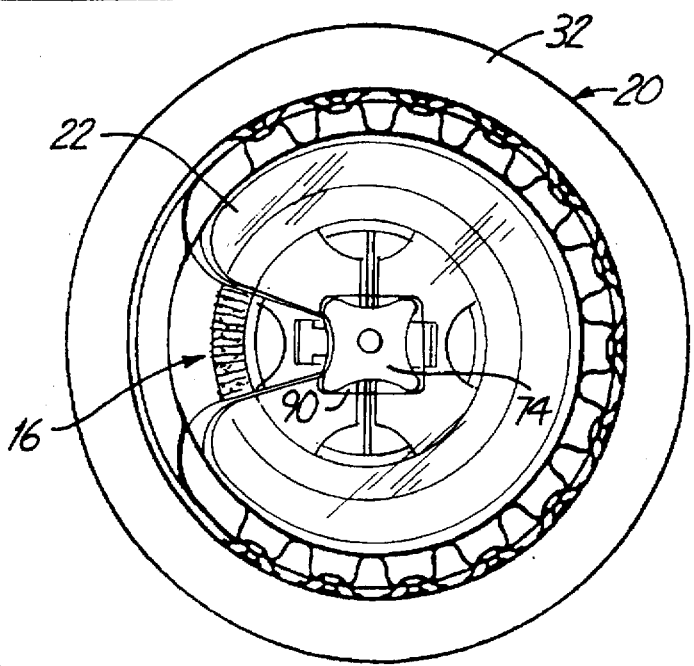
FIG. 7 is a top plan view showing a collar fit into an inner tray in accordance with the present invention.

FIG. 6 is a side elevational view of assembly 10 in an assembled condition and FIG. 7 is a top plan view of inner tray 20 and collar 22 in an assembled condition. As shown in the figures, heart valve prosthesis 16 is securely held in valve holder 14, and valve holder 14 is suspended in inner tray 20. Valve holder 14 is carried in collar 22 at post clamp 86 and on post head support surface 88 shown in FIG. 3A. Post clamp 86 maintains jaws 58 in a position to engage body 52 of prosthesis 16. Rotation stop walls 90 prevent rotation of valve holder 14 by preventing rotational movement of post head tips 92.

Collar 22 is secured in inner tray 20 by lip 84 which is positioned between support surfaces 100 and locking tabs 104. Once positioned, the walls of post clamp 86 receive the radial forces of the positioned collar 22 providing the support necessary to receive shipping and handling forces. Rotation of collar 22 within tray 20 is prevented by key lips 112 which fit in key surfaces 110 of inner tray 20. Middle ledge 108 abuts key lips 112 and prevents rotational movement. V portion 94 allows key lips 112 to be compressed inward, toward each other when collar 22 is inserted in inner tray 20 so that key lips 112 become a locking mechanism between support surfaces 100 and locking tabs 104. Inner tray 20 is sealed by inner tray lid 24.

Inner tray 20 fits in outer tray 18 and is positioned such that tab 48 lies over tab receiving shoulder 46. Outer tray lid 26 seals outer tray 18 and maintains assembly 10 in the position shown in FIGS. 6 and 7.

During surgery, prosthesis 16 is removed in accordance with the following steps. Outer tray lid 26 is removed by pulling on tab 118 which overhangs sealing flange 34. This exposes inner tray lid 24. Inner tray 20 is removed by placing, for example, a thumb and forefinger in finger recesses 40 such that sealing flange 32 of tray 20 is grasped without breaking sterile technique. Alternatively, inner tray 20 can be tipped out from outer tray 18. Furthermore, a tab 130 shown in FIG. 1 can be attached to lid 24 such that a surgeon can grasp tab 130 and lift inner container 20 from outer container 18. Inner tray 20 is then withdrawn from outer tray 18 and outer tray 18 is discarded. Inner tray lid 24 is removed by pulling on tab 48 which extends over flange 32. This exposes post head 74 as shown in FIG. 7. A threaded handle (not shown) may be screwed into threaded receptacle 77 while grasping tray 20. The rounded shape of top concave portion 80 of collar 22 tends to distribute a downward force in an outward, radial direction such that a force may be applied while threading the handle into receptacle 77, without collapsing the collar 22. As described above, rotation of post 68 is prevented by rotation stop walls 90 which lock post 68 in place and by middle ledge 108 and key lips 112 which prevent rotation of collar 22 within tray 20. After the handle is secured to valve holder 14, collar 22 and valve holder 14 may be pulled out of inner tray 20. This snap removal occurs because the tray and collar are preferably made of an elastomeric plastic which allows for moderate deformation.

Removal of collar 22 from inner tray 20 releases the radial forces applied to post clamp 86 and allows for easy removal of valve holder 14 in the surgical setting. Valve holder 14 is removed from collar 22 by grasping collar 22 and sliding post 68 through V portion 94. Valve holder 14 may be moved slightly upward such that post head 74 is above rotation stop walls 90. V portion 94 allows post clamp 86 to spread thereby releasing post 68. Prosthesis 16 is removed from valve holder 14 by cutting a suture (not shown), thereby allowing jaws 58 to move together in an inward direction and be released from body 52.

During implantation, a surgeon may use finger recesses 76 of post head 74 to grasp valve holder 14 and thereby rotate valve body 52. For example, valve body 52 may rotate within suture cuff 50 after suture cuff 50 is attached to the heart tissue annulus. Typically, a surgeon will hold finger recesses 76 between a thumb and opposing forefinger.

Figure 8A:
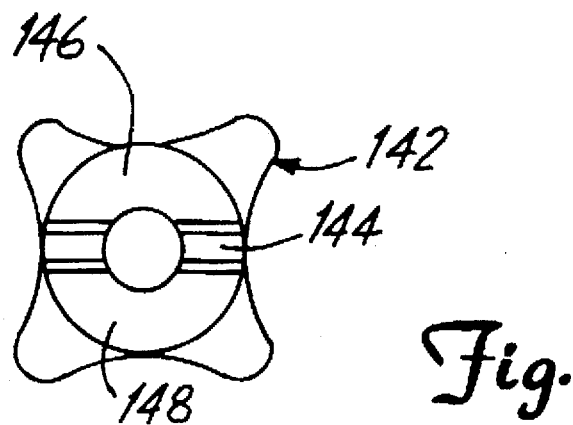
FIG. 8A is a top plan view of a post head design in accordance with another embodiment.
Figure 8B:
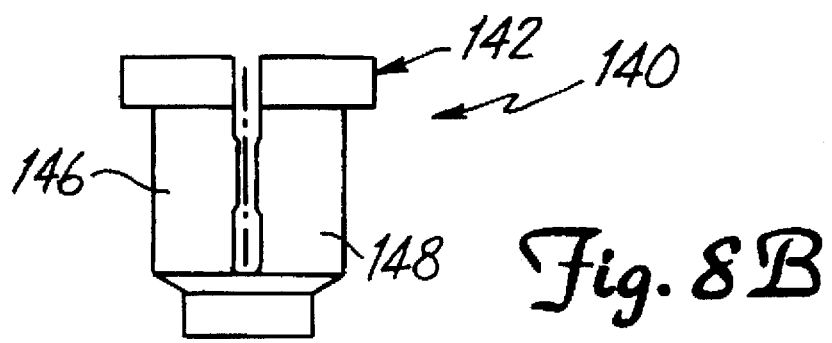
FIG. 8B is a side elevational view of the post in the embodiment of the post head shown in FIG. 8A.

FIG. 8A is a top plan view and FIG. 8B is a side elevational view of another embodiment of post 140 and post head 142. Post 140 is similar to post 68 shown in FIG. 2. Post 140 and post head 142 are designed to receive a snap fit handle (not shown). In such a handle, an elongated post has a cross sectional member. The cross sectional member fits in groove 144 which goes through the center of post 140 and post head 142 and extends in a direction along the axis of post 140. In this design, as the handle is inserted into groove 144, post half 146 and post half 148 move apart along the shaft as the handle enters and is locked in groove 144. The handle and the cross sectional member are locked in place or, snap fit, in groove 144. This requires a downward force while the handle is inserted into groove 144. The rounded shape of top concave portion 80 of collar 22 tends to distribute a downward force in an outward, radial direction such that a force may be applied to snap the handle into groove 144 without collapsing the collar 22.

In a preferred embodiment, trays 18 and 20 and collar 22 are made of a thermal formed polymer, such as polycarbonate, which is clear and which may be steam sterilized. In a preferred embodiment trays 18 and 20 and collar 22 are formed by thermoform molding techniques. Lids 24 and 26 are preferably made from a porous, steam penetrable spun bonded polyolefin material having sterile barrier properties, such as Tyvek® 1073B available from Dupont deNemours, having an adhesive coating. This allows the assembly 10 to be sterilized while in an assembled condition by forcing steam through lids 24 and 26 and across surfaces of the interior of trays 18 and 20 and prosthesis 16. Further, V portion 94 allow steam passage into the inner tray 20. The finger recesses 40 allow pressure to equilibrate between inner tray 20 and outer tray 18 during vacuum steam sterilization.

The packaging is advantageous because the prosthesis 16 is suspended within the packaging and does not contact the sides of the packaging. Further, the packaging is easily disassembled during surgery because the trays are not locked together. Using a clear packaging provides product visibility allowing easy identification of the product. The flexible nature of the tray containers is advantageous because the lips of the containers allow some limited bending of the packaging when a vacuum is applied to the containers during the sterilization process. The locking nature of the components is useful because a rotational torque can be applied without causing the components to slip within each other. The particular packaging is also well suited for low cost, reliable and easy manufacture and provides reduced costs over prior art packaging. The packaging is designed to withstand vacuum steam sterilization, and the pressure differentials imposed during the steam sterilization cycle. In addition, the packaging of the present invention provides dual sterile barriers in a recyclable container. Further, the packaging does not require additional external shock absorbing material such as styrofoam, which allows size reduction. The same snap force which holds the collar in the inner tray prevents the V portion of the collar from spreading, thereby locking the holder in the collar.

FIG. 9 is an exploded perspective view of packaging 200 in accordance with another embodiment. Packaging 200 uses the same outer tray 18 and outer tray lid 26 as shown in FIG. 1. Packaging 200 includes inner container 202 and inner container lid 204. Container 202 includes threading 206 such that lid 204 can be screwed onto container 202, thereby sealing container 202. Container 202 is of size and shape to carry a tissue heart valve (not shown) or other bioprosthetic. Container 202 fits into recess 28. Lid 26 is heat sealed to outer tray 18. A spacer 212 made of shock absorbing material may be included within recess 28, such as a foam or styrofoam material. Spacer 212 fits between lids 204 and 26 and protects lid 26 from damage from lid 204.

Finger recesses 40 are provided such that container 202 and lid 204 can be grasped between an opposing finger and thumb of a surgeon. Additionally, container 202 can be removed from container 18 by grasping the outer circumference of container 18 and tipping container 18.

In the present invention, the product is suspended in the inner tray using a locking mechanism which uses the combined forces from the post, collar and inner tray. The retaining shelf and bumps of the inner tray form upper and lower restraints which prevent upward or downward movement of the collar. The locking mechanism which is utilized to suspend the product within the package functions without any input from the outer tray. This allows the outer tray to function as a shock absorber without effecting the contained product. Additionally, the design of the locking mechanism transmits absorbed forces primarily in radial directions towards the inner tray walls, as opposed to directing the forces towards the seal used to maintain the sterile barrier. The design is robust and well suited for transportation and storage. The ability to open the package and present it to the sterile field during surgery without breaking sterile technique is considerably easier than in prior art techniques due to the finger recesses in the outer package and the fact that the inner tray is not "locked" within the outer tray.

Although the present invention has been described with reference to preferred embodiments, workers skilled in the art will recognize that changes may be made in form and detail without departing from the spirit and scope of the invention. For example, the holder may be of any desired shape to fit within the collar. Furthermore, other post head configurations may be used in which rotation of the post is prevented. Additionally, other types of heart valves, such as aortic heart valves, and holders and heart valve prostheses of any design from any manufacturer other than those specifically shown may also be used with the present invention. Holder 14 and prosthesis 16 are provided as example configurations.

What is claimed is:

1. An apparatus for carrying a heart valve prosthesis, comprising:
   an outer tray having a recess formed therein and a sealing flange;
   an inner tray having a recess formed therein and a sealing flange, the inner tray shaped to fit in the recess of the outer tray;
   a heart valve prosthesis holder adapted to carry the heart valve prosthesis;
   a collar adapted to carry the holder and shaped to fit in the inner tray whereby the heart valve prosthesis is suspended in the recess of the inner tray, the collar having a concave top to distribute a downward force to the top of the collar in a radial direction;
   an inner tray lid sealed to the sealing flange of the inner tray; and
   an outer tray lid sealed to the sealing flange of the outer tray.

2. The apparatus of claim 1 wherein the holder includes a post and the collar includes a post clamp to secure the post therein.

3. The apparatus of claim 2 wherein the holder includes jaws for grasping the prosthesis and the post clamp maintains the jaws in position to engage the prosthesis.

4. The apparatus of claim 2 wherein the post includes a post head and the collar includes a post head support surface for receiving the post head.

5. The apparatus of claim 2 wherein the post includes a post head having a post head tip extending radially and the collar includes a locking mechanism which engages the post head tip to thereby prevent rotation of the holder.

6. The apparatus of claim 1 wherein the collar includes a collar lip and the inner tray includes a collar support surface to support the collar lip.

7. The apparatus of claim 6 wherein the inner tray includes a collar lock tab positioned adjacent the collar support surface to lock the collar lip therebetween.

8. The apparatus of claim 7 including a plurality of collar lock tabs and a plurality of collar support surfaces circumferentially interspersed therebetween.

9. The apparatus of claim 1 wherein the collar includes key lips and the inner tray includes a ledge adapted to fit between the key lips and thereby prevent rotation of the collar in the inner tray.

10. The apparatus of claim 1 wherein the inner tray includes an inner tray flange and the outer tray includes a flange shoulder to support the inner tray flange thereon.

11. The apparatus of claim 1 wherein the outer tray includes a finger recess to provide access to the inner tray such that a surgeon can grasp the inner tray.

12. The apparatus of claim 1 wherein the inner tray lid includes a tab for grasping to remove the inner tray lid from the inner tray and the outer tray includes a tab receiving shoulder for supporting the tab.

13. The apparatus of claim 1 wherein the inner tray lid and the outer tray lid are steam penetrable whereby the apparatus and prosthesis may be sterilized by application of steam in conjunction with vacuum forces.

14. The apparatus of claim 13 wherein the inner tray lid and the outer tray lid are sealed at flexible flanges allowing limited deformation in response to the vacuum forces.

15. The apparatus of claim 1 wherein the inner tray, outer tray and collar comprise a clear polymer.

16. The apparatus of claim 1 wherein the inner tray, outer tray and collar are formed by thermoform molding.

17. The apparatus of claim 1 wherein the holder includes a post having a post head with finger grips formed therein.

18. An apparatus for carrying a heart valve prosthesis, comprising:

a first tray having a recess formed therein and a collar support surface, the tray including at least one collar lock tab adjacent the support surface and forming a space therebetween;

a holder for holding the prosthesis, the holder having an elongated post and jaws coupled to the post adapted for grasping the prosthesis; and a collar having a post clamp adapted to releasable hold the post of the holder, the collar configured to fit and be positioned on the collar support surface of the first tray, whereby the prosthesis is suspended by the holder in the recess of the first tray, wherein the post clamp maintains the jaws of the holder in a position to engage the prosthesis, the collar further comprising a collar lip adapted to fit in the space between the at least one collar lock tab and the collar support surface, thereby securing the collar in the first tray.

19. The apparatus of claim 18 including a plurality of collar lock tabs adjacent the collar support surface forming a space therebetween and a plurality of collar support surfaces circumferentially interspersed therebetween.

20. The apparatus of claim 18 wherein the collar further comprises key lips and the first tray further comprises a ledge adapted to fit between the key lips, thereby preventing rotation of the collar in the first tray.

21. The apparatus of claim 18 further comprising a second tray having a recess formed therein, the first tray shaped to fit within the second tray.

22. The apparatus of claim 18 wherein the post includes a post head having a post head tip extending radially and the collar includes a locking mechanism which engages the post head tip to thereby prevent rotation of the holder.

23. The apparatus of claim 18 wherein the collar has a concave top to distribute a downward force applied to the top of the collar in a radial direction.

24. The apparatus of claim 18 wherein the collar has an opening, such that the post of the holder can slide through the opening so that the holder be released from the collar.

25. An apparatus for carrying a heart valve prosthesis, comprising:

a first tray having a recess formed therein and a collar support surface;

a holder for holding the prosthesis, the holder having an elongated post, the post including a post head having a post head tip extending radially; and a collar having a post clamp adapted to releasably hold the post of the holder, the collar configured to fit and be positioned on the collar support surface of the first tray, whereby the prosthesis is suspended by the holder in the recess of the first tray, and the collar includes a locking mechanism which engages the post head tip to thereby prevent rotation of the holder relative to the collar.

26. The apparatus of claim 25 wherein the holder includes jaws for grasping the prosthesis and the post clamp holds the jaws in position to engage the prosthesis.

27. The apparatus of claim 25 wherein the collar includes a post head support surface for receiving the post head.

28. The apparatus of claim 25 wherein the collar has a concave top to distribute a downward force applied to the top of the collar in a radial direction.

29. The apparatus of claim 25 wherein the collar includes a collar lip and the first tray includes a collar support surface to support the collar lip.

30. The apparatus of claim 29 wherein the first tray includes a collar lock tab positioned adjacent the collar lip to lock the collar lip therebetween.

31. The apparatus of claim 25 wherein the collar includes key lips and the first tray includes a ledge adapted to fit between the key lips and thereby prevent rotation of the collar in the first tray.

32. The apparatus of claim 25 including a second tray receiving the first tray therein, wherein the first tray includes a first tray flange and the second tray includes a flange shoulder to support the first tray flange thereon.

33. The apparatus of claim 25 wherein the a post head has finger grips formed therein.

* * * * *

UNITED STATES PATENT AND TRADEMARK OFFICE
CERTIFICATE OF CORRECTION

PATENT NO. : 5,720,391
DATED : February 24, 1998
INVENTOR(S) : Neil P. Dohm et al.

It is certified that error appears in the above-identified patent and that said Letters Patent is hereby corrected as shown below:

Col. 7, line 48, change "releasable" to --releasably--.

Col. 8, line 57, delete "a".

Signed and Sealed this

Tenth Day of November 1998

Attest:

BRUCE LEHMAN

Attesting Officer     Commissioner of Patents and Trademarks